United States Patent
Lajoie et al.

(10) Patent No.: US 9,934,360 B2
(45) Date of Patent: Apr. 3, 2018

(54) DENTAL DATA PLANNING

(75) Inventors: Jean-Philippe Lajoie, Quebec (CA); David Giasson, Quebec (CA)

(73) Assignee: Biocad Medical, inc., Quebec City (CA)

( * ) Notice: Subject to any disclaimer, the term of this patent is extended or adjusted under 35 U.S.C. 154(b) by 483 days.

(21) Appl. No.: 12/703,596

(22) Filed: Feb. 10, 2010

(65) Prior Publication Data

US 2011/0196653 A1    Aug. 11, 2011

(51) Int. Cl.
| | |
|---|---|
| *G06Q 50/00* | (2012.01) |
| *G06Q 10/00* | (2012.01) |
| *G06F 19/00* | (2018.01) |
| *A61C 9/00* | (2006.01) |
| *A61C 13/00* | (2006.01) |

(52) U.S. Cl.
CPC .......... *G06F 19/3437* (2013.01); *A61C 9/004* (2013.01); *A61C 13/0004* (2013.01)

(58) Field of Classification Search
CPC .. A61C 13/0004; A61C 7/002; G06F 19/3437
USPC ............................................ 705/2–3; 433/24
See application file for complete search history.

(56) References Cited

U.S. PATENT DOCUMENTS

| | | | |
|---|---|---|---|
| 4,575,805 A | 3/1986 | Moermann et al. | |
| 5,027,138 A | 6/1991 | Gandrud | |
| 5,675,069 A | 10/1997 | Schleupen et al. | |
| 6,099,314 A | 8/2000 | Kopelman et al. | |
| 6,179,611 B1 | 1/2001 | Everett et al. | |
| 6,227,850 B1 * | 5/2001 | Chishti et al. ................... | 433/24 |
| 6,334,772 B1 | 1/2002 | Taub et al. | |
| 6,463,344 B1 | 10/2002 | Pavloskaia et al. | |
| 6,592,371 B2 | 7/2003 | Durbin et al. | |
| 6,648,640 B2 | 11/2003 | Rubbert et al. | |
| 6,664,986 B1 | 12/2003 | Kopelman et al. | |
| 6,665,570 B2 | 12/2003 | Pavloskaia et al. | |
| 6,705,863 B2 | 3/2004 | Phan et al. | |
| 6,767,208 B2 | 7/2004 | Kaza | |
| 6,882,894 B2 | 4/2005 | Durbin et al. | |
| 6,947,038 B1 | 9/2005 | Anh et al. | |
| 7,013,191 B2 | 3/2006 | Rubbert et al. | |
| 7,029,275 B2 | 4/2006 | Rubbert et al. | |
| 7,069,850 B2 | 7/2006 | Nakamura et al. | |
| 7,080,979 B2 | 7/2006 | Rubbert et al. | |
| 7,118,375 B2 | 10/2006 | Durbin et al. | |
| 7,156,655 B2 | 1/2007 | Sachdeva et al. | |
| 7,220,124 B2 | 5/2007 | Taub et al. | |

(Continued)

FOREIGN PATENT DOCUMENTS

WO       WO 00/08415       2/2000

*Primary Examiner* — Christopher L Gilligan
(74) *Attorney, Agent, or Firm* — Knobbe Martens Olson & Bear LLP (57) ABSTRACT

Presented herein are methods, systems, devices, and computer-readable media for dental data planning. In various embodiments, an operator of the system can design a dental data plan, have it checked, and see various aspects of the plan on the display. The plan may be designed in the abstract and that abstract plan can be checked for compliance with material and product constraints. Also from that abstract plan, a list of necessary scanning tasks may be produced and displayed. In some embodiments, plans for multiple patients can be designed and the scanning for those patients may commence before all of the patients are completed.

55 Claims, 10 Drawing Sheets

(56) References Cited

U.S. PATENT DOCUMENTS

| | | | |
|---|---|---|---|
| 7,322,824 B2* | 1/2008 | Schmitt | A61C 13/0004 |
| | | | 433/215 |
| 7,590,462 B2 | 9/2009 | Rubbert et al. | |
| 7,717,708 B2 | 5/2010 | Sachdeval et al. | |
| 8,021,147 B2 | 9/2011 | Sporbert et al. | |
| 8,121,718 B2 | 2/2012 | Rubbert et al. | |
| 8,177,551 B2 | 5/2012 | Sachdeva et al. | |
| 2001/0021498 A1* | 9/2001 | Osorio et al. | 433/173 |
| 2003/0039389 A1 | 2/2003 | Jones et al. | |
| 2003/0232302 A1 | 12/2003 | Babayoff et al. | |
| 2003/0235803 A1* | 12/2003 | Nikolskiy et al. | 433/213 |
| 2004/0081938 A1 | 4/2004 | Chishti et al. | |
| 2005/0186540 A1 | 8/2005 | Taub et al. | |
| 2006/0115793 A1 | 6/2006 | Kopelman et al. | |
| 2006/0275736 A1 | 12/2006 | Wen et al. | |
| 2006/0275737 A1 | 12/2006 | Kopelman et al. | |
| 2008/0261165 A1 | 10/2008 | Steingart et al. | |
| 2009/0248184 A1* | 10/2009 | Steingart et al. | 700/98 |
| 2009/0286196 A1* | 11/2009 | Wen et al. | 433/24 |
| 2009/0325128 A1 | 12/2009 | Holzner et al. | |
| 2010/0003635 A1 | 1/2010 | Feith | |
| 2010/0281370 A1 | 11/2010 | Rohaly et al. | |
| 2011/0105894 A1* | 5/2011 | Kopelman et al. | 600/425 |
| 2011/0196524 A1 | 8/2011 | Giasson et al. | |
| 2011/0196653 A1 | 8/2011 | Lajoie et al. | |
| 2011/0196654 A1 | 8/2011 | Genest et al. | |
| 2011/0224955 A1 | 9/2011 | Fisker et al. | |
| 2011/0295402 A1 | 12/2011 | Dumitrescu et al. | |
| 2012/0015328 A1 | 1/2012 | Giasson et al. | |
| 2012/0022834 A1 | 1/2012 | Lajoie-Dorval | |
| 2012/0070803 A1 | 3/2012 | Manai et al. | |
| 2012/0072177 A1 | 3/2012 | Manai et al. | |
| 2012/0072178 A1 | 3/2012 | Beaudry et al. | |

\* cited by examiner

DENTAL DATA PLANNING

BACKGROUND

Field

The present application generally relates to dental prosthetics, and more particularly to user interfaces and associated technology for dental data planning.

Description of Related Technology

In recent years, dental prosthetic design has been accomplished increasingly using computer systems and 3D computer graphics or CAD (computer-aided design) software. These systems allow a dentist, dental technician, or other operator to design dental prosthetics for individual patients. These individual prosthetic designs are often called "situations," "dental plans," or "prosthetic plans." The case designs that are made in the 3D or CAD software are typically based on the scans of the patient's teeth, gums, and bone structure as well as on a library of the teeth shapes and positions, available dental hardware, and system constraints. Once the dentist has loaded all of the relevant data for the patient, she can begin to refine the plan.

A problem with such 3D design systems is that they require a great deal of underlying dental data. This dental data may include 3D models built from scans of the preparations, gums, models or wax-ups, implant replicas, or other patient data as well as aspects of the desired prosthetic design or dental plan. The reason for the potentially large number of scans is that some software systems operate based on the relative locations of the bone, gum lines, example or desired prosthetic positions, and implant anchor locations. Limitations of the scanner, such as the scanning volume, can also increase the number of scans needed. Designing based on this patient-specific data is desirable in order to improve the dental plan. For example, desired symmetry with neighboring teeth and relative bite placement helps define the functional and aesthetic aspects of the dental plan.

Obtaining all of this patient-specific data can be time consuming and difficult to both plan and execute. It is not hard to imagine a dentist or dental technician who scans a number of aspects of patient-specific data, loads this data into the 3D or CAD software, begins to work on refining and manipulating the dental plan, and then realizes that she has not scanned in all the necessary aspects or components of the underlying patient-specific data. She may then have to return to the scanner and scan in the missing elements. Further, for many systems, the relative locations of the patient-specific data are important. Therefore, if you miss even a single scan, you may have to restart scanning all over again. For example, if designing the dental data plan would require a scan of the wax-up and multiple implant locations and the operator missed scanning a single implant location, then she may have to start the scanning process all over again because, even if she later scans the missing implant, the system can't determine that implant's location relative to the other scanned components. These issues can break up the design process and can cause great inefficiencies.

There may be a number of physical constraints on the individual aspects of the situation or case design. For example, certain materials may fail or otherwise be unavailable for a bridge framework that spans beyond a threshold number of teeth. In traditional systems, a dentist may design a case, situation, or dental plan and send it off to the manufacturer. If the case design, situation, or dental plan does not meet the manufacturer's specification, the manufacturer may flag it and inform the dentist or may build the situation even though it might fail. If the manufacturer constructs and sends the situation to the dentist, then the dentist may see it fail either in installation or use. These failures may result in much wasted time, effort, and money.

Dental technicians and other professionals may be presented with multiple, similar cases and design multiple, similar case designs or dental data plans. The case designs may all be for separate patients and the dental technician may design each one separately. The dental technician may, for example, design one case, perform the necessary scanning steps, and then start again with the next case. Designing each of these similar cases separately may prove inefficient because of the overlap of necessary types of scans and other aspects of the design process.

Another problem with traditional systems is that the techniques and knowledge about available dental hardware is kept separate from the techniques and knowledge of what is needed for dental data plans, and both are kept separate from the knowledge of what scanning is needed.

These problems and others are addressed by the systems, methods, and devices and computer-readable media described herein

SUMMARY

Presented herein are methods, systems, devices, and computer-readable media for dental data planning. The summary in this section does not define or limit the invention, but instead merely provides insight into some of the embodiments.

In some embodiments, dental data planning data systems, methods, and computer-readable media include receiving, from an operator, at a computer system, via a computer-implemented user interface, information about a desired dental data plan for a patient. The system may then determine whether the desired dental data plan is valid. If the desired dental data plan is valid, scanning steps necessary to enact that plan may be determined. The scanning determined scanning steps may then be displayed to the user via the user interface.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION OF SPECIFIC EMBODIMENTS

Overview

In the field of dental prosthetic case design, as noted herein, coordinating the preparations for a case can be complex and time consuming. In order to later use CAD or 3D prosthetic design software to refine a case, shape a prosthetic, etc., it is necessary to have the underlying data in place. This data can include a number of things. For example, the dentist, dental technician, or other practitioner (hereinafter called "operator") may have to perform a number of 3D scans of the bones, gums, implants, wax-up models, preparations, dental models or patients' oral anatomy, etc. Without proper preparation, the operator, when she later works on the case design in 3D or CAD design software, may find that she did not have all of the underlying data that she needs in order to properly design the case. Examples of CAD and 3D design software are given in U.S. patent application Ser. No. 12/703,601, entitled Dental Prosthetics Manipulation, Selection, and Planning, filed concurrently herewith, the contents of which are hereby incorporated by reference in their entirety for all purposes.

Various embodiments of the systems herein help coordinate and prepare the data for later case designs. For example, if an operator is working on a single case, she may want to make a bridge or bridge framework for a patient from tooth position 25 to tooth position 27 and may know the material of the bridge or framework. Various embodiments herein, such as that depicted with respect to FIG. 1, and which is discussed in more detail herein, may allow her to specify the bridge, its location, and its material by first selecting a type of crown, bridge framework, abutment, or other object in the patient information portion 140. Then she can select one or more tooth positions (e.g., tooth positions 25 to 27) on which to place the crown, bridge framework, etc. in the desired dental data portion 150. Once the crown, bridge framework, etc. has been added to the desired dental plan, she may see, in various embodiments, a list of related, needed scans in the scanning task list portion 130. This is a list of scans that are required to complete the desired dental data plan. The system may walk her through scanning those steps—either while she is still adding components to the desired dental data plan or once she has completed the planning process. She may also see, in various embodiments, that there is a list of components in the components portion 160. The components listed in the components portion 160 may include prosthetics and other components for which she can define material properties, material shade, etc. The operator can define these materials and the system can check whether the materials are valid. For example, some materials from which bridge frameworks are made can only span a certain number of tooth positions. If the operator has added a bridge framework and defined its material and the bridge framework in that material would be invalid, that invalidity may be indicated by the system to her so that she may correct it.

Figure 2:
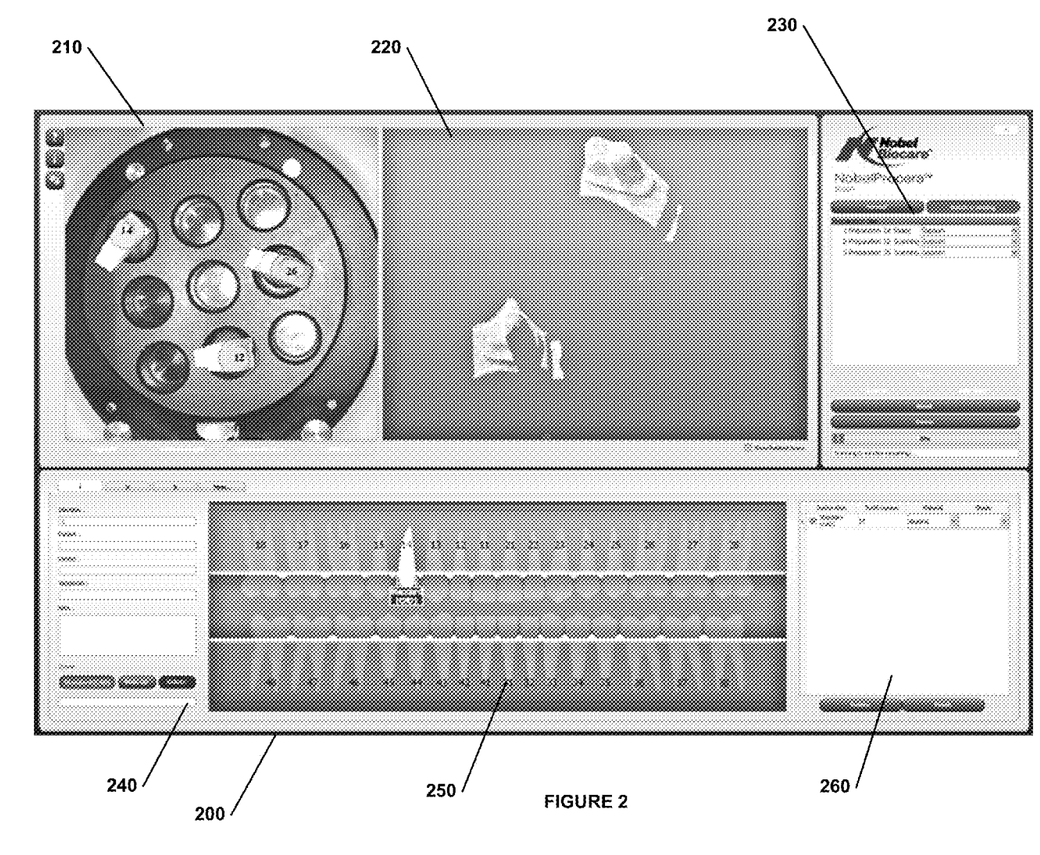
FIG. 2 is an illustration of a second exemplary display for dental data planning.

Some embodiments herein will help an operator plan case designs for multiple patients. For example, an operator may wish to design three single-tooth cases for three different patients. Embodiments herein may allow the operator to plan and prepare for all three cases efficiently by providing a separate plan for each case, but advising the operator of the necessary scans and viability of the individual plans, all within a single system. One example embodiment of this is shown in FIG. 2, which is discussed in more detail herein.

Figure 3:
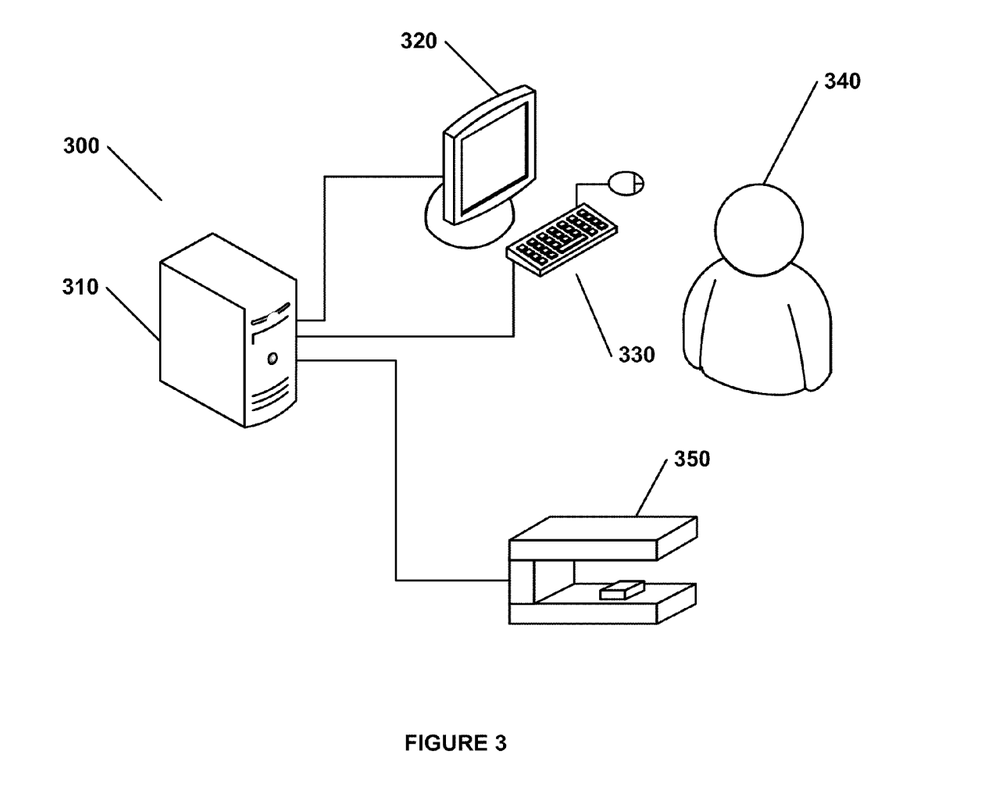
FIG. 3 illustrates an exemplary system for dental data planning.

Various embodiments of the system may be built on one or more computer systems, such as system 300, described herein with respect to FIG. 3. Further discussions of embodiments are given herein with respect to FIGS. 1-10.

As used herein, the phrase "dental data plan" may refer to the data that is needed by a later dental design system. It may include patient-specific scans, prosthetics, or anything else that is needed by dental design software.

Exemplary System

FIG. 3 illustrates an exemplary system 300 for dental data planning. The system 300 may include one or more computers 310 coupled to one or more displays 320, one or more input devices 330, and one or more scanners 350, such as a 3D scanner. An operator 340, who may be a dentist, dental technician, or other person, may plan the data for dental prosthetics using system 300 by manipulating the one or more input devices 330, which may be a keyboard and/or a mouse. In some embodiments, while working on the dental data plan, the operator 340 may see the plan on the display 320. The display 320 may include two or more display regions or portions of the display, each of which displays a different aspect of the dental data plan. For example, in some embodiments, the display 320 may show a case designer for indicating and modifying the general dental data plan, a list of the scans that need to take place for the dental data plan and their statuses, a list of products that will be needed for the dental data plan and an indication of the viabilities of using those products for the dental data plan, a video or image of an object in the scanner 350, and/or a rendering of the 3D surface just scanned, possibly with the 3D surfaces of previous scans being displayed as well. The display 320 may also have an area that would allow the operator 340 to input patient(s) data, which the operator could input using input devices 330, such as a keyboard and mouse.

After the dental data plan preparation is completed, in whole or in part, the operator 340 may be prompted to place a first object such as a dental model, impression tray, or an imprint of the patient's anatomy (gums, teeth, etc.) into scanner 350. This first object may be at least a portion of the model of the patient, perhaps on a holder or gypsum base, as depicted in the scanner video portion 110 in FIG. 1. When prompted to do so by the display 320, the operator 340 may add the next needed object, such as a dental plan wax-up or implant replica, etc., to the holder or gypsum base and placing the model into the scanner 350. Other orders and forms of placing objects in the scanner may also be used. In various embodiments, after each object has been added to the scanner 350, it can then proceed with the scanning of the object, and the operator 340 can proceed with designing parts of the dental data plan using system 300 or await the results of the scan. These and other possible embodiments are discussed in more detail herein.

In various embodiments, the computer 310 may include one or more processors, one or more memories, and/or one or more communication mechanisms. In some embodiments, more than one computer 310 may be used to execute the modules, methods, and processes discussed herein. Additionally, the modules and processes herein may each run on one or multiple processors, on one or more computers; or the modules herein may run on dedicated hardware. The input devices 330 may include one or more keyboards (one-handed or two-handed), mice, touch screens, voice commands and associated hardware, gesture recognition, or any other means of providing communication between the operator 340 and the computer 310.

The display 320 may be a 2D or 3D display and may be based on any technology, such as LCD, CRT, plasma, projection, et cetera. The scanner 350 may be a 2D or 3D scanner. In some embodiments, 3D scanning in scanner 350 is accomplished using time-of-flight calculations, triangulation, conoscopic holography, structured light, modulated light, computed tomography, microtomography, magnetic resonance imaging, or any appropriate technology or technique. In some embodiments, 3D scanner may use x-rays, visible light, laser light, ultrasound radiation, or any other appropriate radiation or technology. In some embodiments, the 3D scanner may use stereoscopy, photometry, silhouetting, touch probe, or any other appropriate technique.

The communication among the various components of system 300 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 300 may also be combined into a single unit. In some embodiments, all of the electronic components of system 300 are included in a single physical unit.

Dental Data Planning

Figure 4:
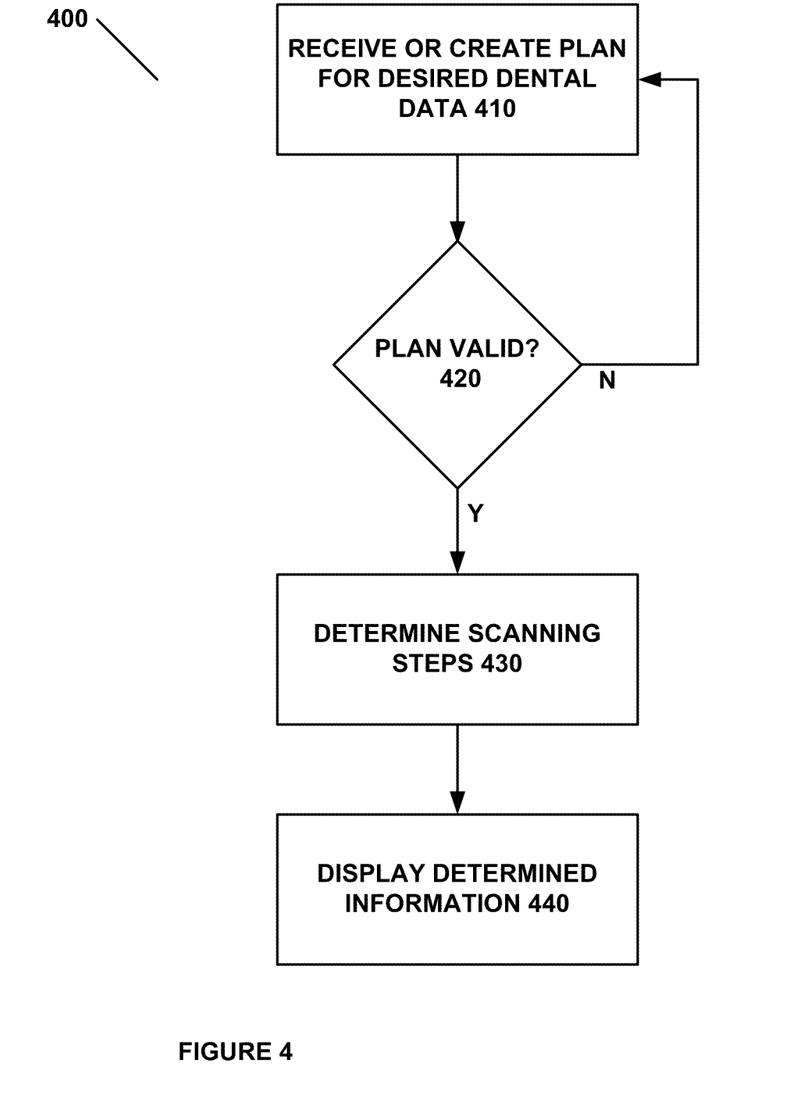
FIG. 4 illustrates a flow diagram for an exemplary method for dental data planning.
Figure 5:
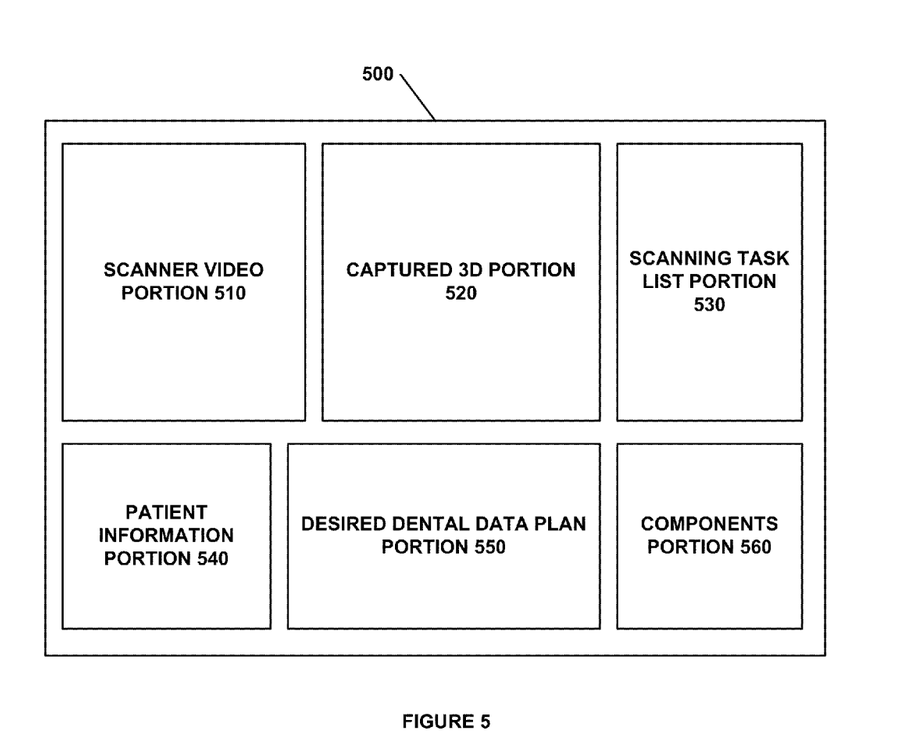
FIG. 5 is an illustration of a third exemplary display for dental data planning.

FIG. 4 illustrates a flow diagram for an exemplary method 400 for performing the steps of dental data planning. FIG. 5 is an illustration of a third exemplary display 500 for dental data planning. The process of FIG. 4 will be described primarily with respect to FIG. 5. Briefly describing FIG. 5, a display 500 may include numerous displays, sub-displays, windows, graphical user interface elements, or portions 510-560 of a display 500. Each of the numerous portions 510-560 may be displayed on a single physical display, such as display 320 of FIG. 3, or on multiple physical displays 320 in system 300 of FIG. 3 (not pictured).

In the example embodiment of FIG. 5, display 500 includes a scanner video portion 510, which may display a real-time or near real-time video or an image of an object in a scanner, such as scanner 350 of FIG. 3. The captured 3D portion 520 may display a 3D model or 3D data that is derived from data captured by scanner 350 of FIG. 3. The scanning task list portion 530 may include a list of scans that need to be performed for the dental data plan that has been designed, for example, by operator 340 using system 300. The patient information portion 540 may provide for inputting patient name, selecting types of objects to add to the dental data plans (such as abutments, crowns, wax-ups, cut backs, anatomic features, preparation lines, gums, implants, bite indices, diagnostic data, etc.). The desired dental data portion 550 may include an abstract display of the dental data plan as it currently stands as well as allow, with operator input, the manipulation of the dental data plan. The dental data plan may be displayed, in desired dental plan portion 550, in a cross-section of all or various tooth positions in a human mouth in a non-overlapped fashion, including the various components added to the dental data plan. As an example of manipulating the dental data plan, an operator may be able to add components, such as an abutment, to a dental data plan by selecting the type of abutment from the patient information portion 540 and indicating with a mouse or other input device where to place the abutment in the desired dental data plan portion 550. The components portion 560 may include a list of the components that are needed in order to obtain the dental data in the desired dental data plan portion 550.

Figure 7:
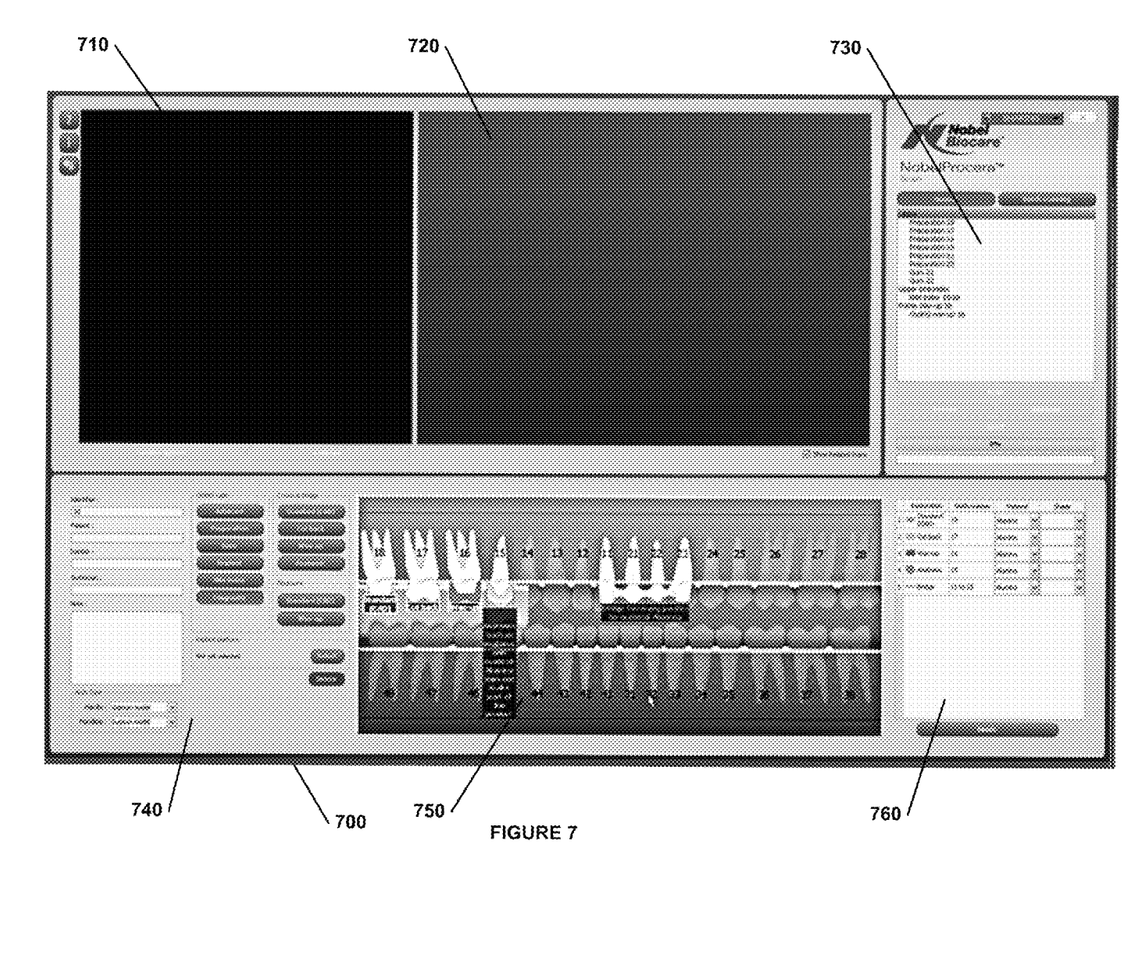
FIG. 7 is an illustration of a fourth exemplary display for dental data planning.
Figure 8:
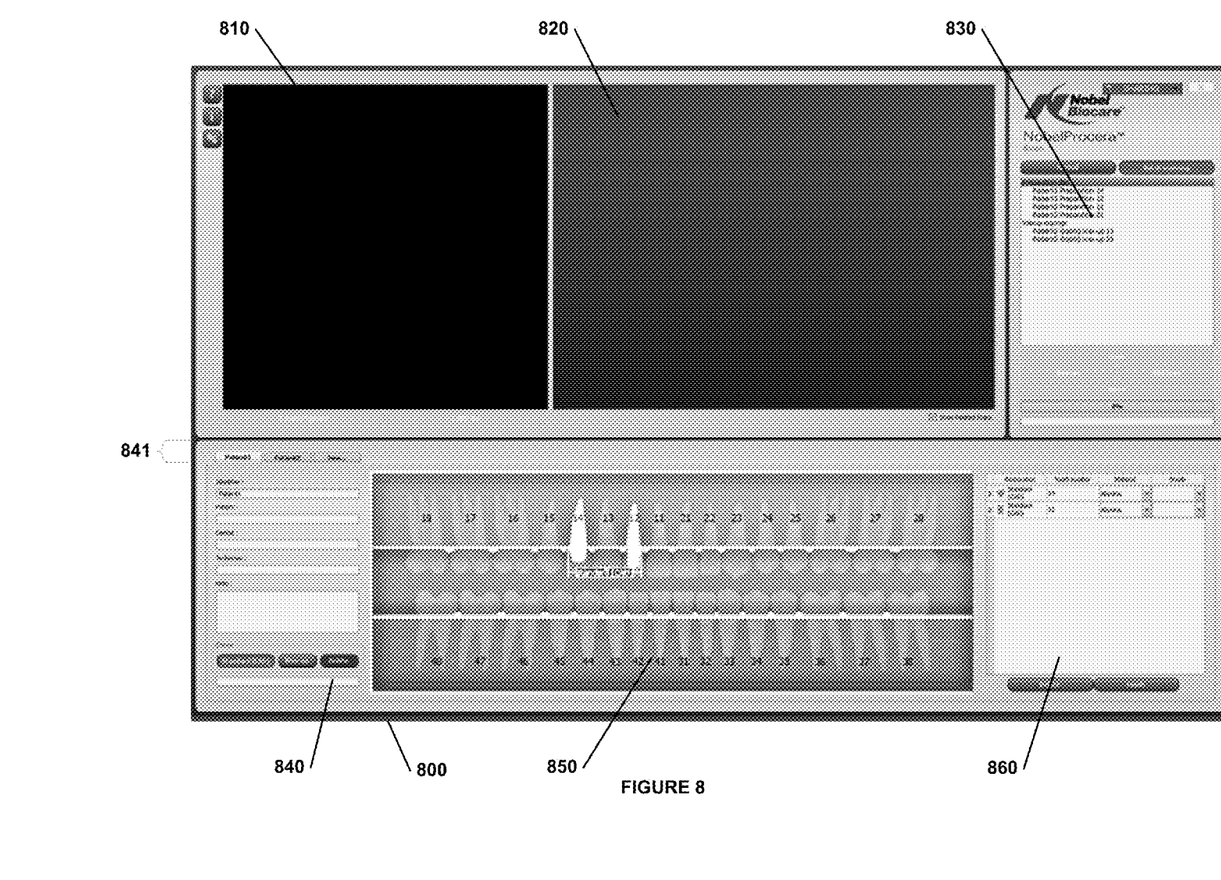
FIG. 8 is an illustration of a fifth exemplary display for dental data planning.

In some embodiments, only a subset of portions 510-560 is included in display 500. For example, an embodiment may not have a scanner video portion 510. In some embodiments, more portions which are not depicted in display 500 are included in display 500. For example, there may be multiple patient information portions 540, one for each patient, and they may or may not be overlapped. FIGS. 7 and 8 depict fourth and fifth examples of a display with portions 710-760 and 810-850, respectively.

Returning now to FIG. 4, a plan for the desired dental data is received or created in step 410. In some embodiments, the desired dental data plan may initially be empty or blank and the operator may create the plan for the dental data by interacting with the display 500. For example, an operator may start with a blank plan and create a plan for the desired dental data using the patient information portion 540 and desired dental data plan portion 550 described herein with respect to FIG. 5. On the other hand, a general template of a dental data plan or a plan specific to an operator may be uploaded or downloaded locally or from a remote location. An operator may manipulate this obtained dental data plan using the patient information portion 540 and the desired dental data plan portion 550. For example, an operator may add an abutment to the plan by selecting a button in patient information portion 540 and define the tooth position for the abutment in the desired dental data plan portion 550.

In step 420, the validity of desired dental data plan is checked. The validity of the plan may be checked when it is modified or upon some other action, such as a button press, occurrence of a hardware or software interrupt or event, or the passage of a certain amount of time. In some embodiments, the constraints that are checked as part of a validity determination may include the physical constraints on the types of materials and/or product constraints for the various aspects of the desired dental data plan. For example, if an operator has added a bridge framework that spans multiple teeth and selected a particular product for that bridge framework, then the system may check whether that product is available in the desired tooth span and whether the material that makes up the product is capable of such a span or recommended for such a span. In some embodiments, the constraints checked will also include other constraints, such as the availability of inventory for the desired products or materials. Other example constraints may, in various embodiments, include:

When planning an implant-supported prosthesis, ensuring that the implant connection interface is defined.

When planning a tooth-supported restoration, a gum, or an implant, ensuring an accompanying prosthetic element is defined.

When defining a prosthetic element, ensuring the production material is defined.

When several shades are available for a specific material, ensuring that a shade is selected.

Ensuring that a defined restoration fulfills production constraints, such as:
  Maximum number of units.
  Maximum number of implants.
  Minimum number of implants.
  Maximum number of pontics.
  Maximum number of pontics in a row.

Maximum number of cantilever pontics.
Avoiding unconnected pontics.
Ensuring that materials that are only allowed for certain tooth positions in the jaw are not used outside of those positions.
Checking for limitations of the dental design software, such as CAD software, if the desired software is known. These may include for various programs constraints such as:
One implant bridge per case design or dental data plan.
One bar per case design or dental data plan.
No mixing of different restoration types in the same situation.
Checking for the availability of the product in the product catalogue and whether the product is available in a specific market.

If some aspect of the plan does not meet the constraints, then, in some embodiments, the display 500 may show an indication related to the failed constraint and allow the operator to fix the plan by returning to step 410. In some embodiments, this indication may be shown immediately or upon completion of various steps, as described with respect to step 440.

If the plan is valid in light of the constraints, then in step 430, the scanning steps needed for the desired dental data plan are determined. As an example, consider a dental data plan in which a bridge and a crown are all being designed for the patient. Each of those parts of the plan may require certain scans and they are determined in step 430. In some embodiments, the determined scanning task list is displayed, as depicted in FIG. 7, where the scanning task list portion 730 includes a list of scans that must be accomplished in order to have all of the desired dental data in the plan. There may be needed, for example, a scan of each preparation, scans of the gums in the locations spanned by the bridge framework, an opposing bite index, and a wax up, as depicted in portion 730 of FIG. 7.

In some embodiments, the scans needed for each particular plan will depend upon the dental data plan itself and the desired output. For example, if the desired output should include data for the opposing bite, then a model or impression of the opposing jaw will need to be scanned. If the desired plan requires knowing the spatial locations of implants, then it may be necessary to scan those implant replicas (possibly with an implant locator). If the desired plan includes a bridge framework, then the gums below the bridge framework may need to be scanned. If a plan includes affixing to bone, such as for planning of implant placement, then a scan of the bone may be needed. Other types of scans and their necessities will be known to those skilled in the art.

Figure 9:
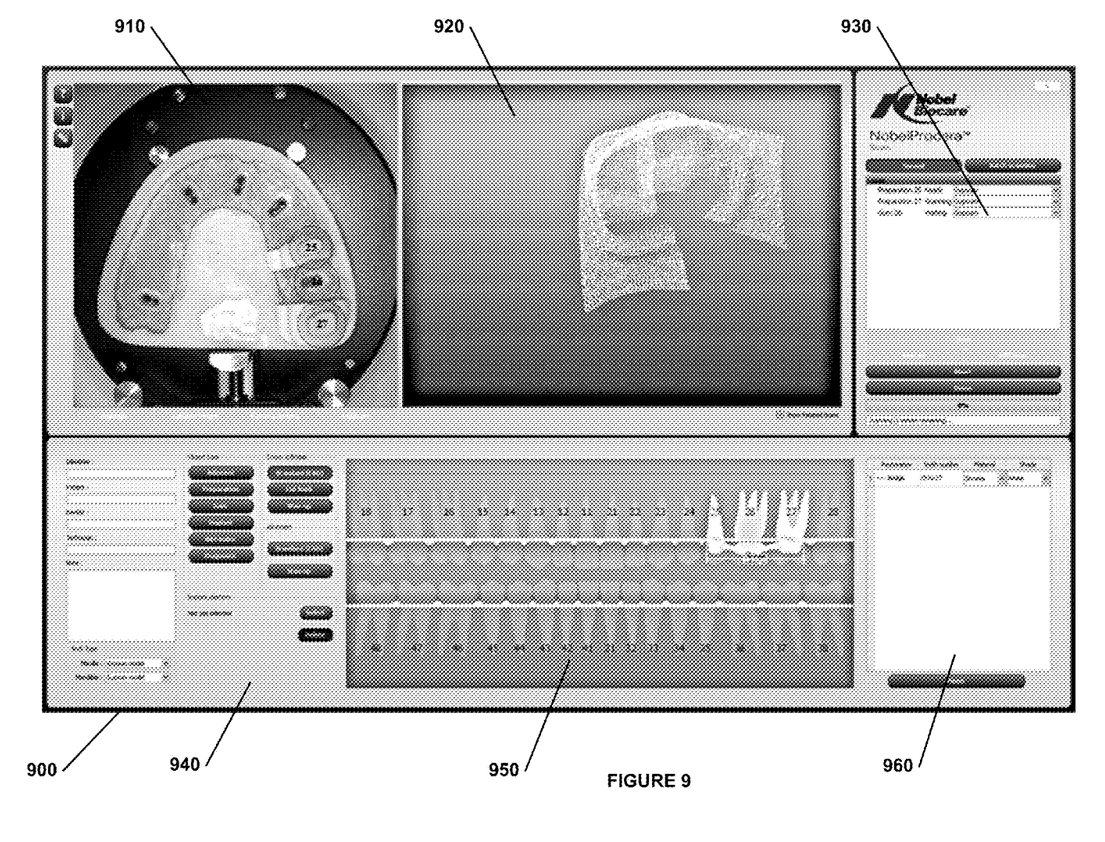
FIG. 9 is an illustration of a sixth exemplary display for dental data planning.

The information that has been determined is displayed in step 440. For example, if the dental data plan is valid (per step 420), then the dental data plan may be shown in the desired dental data portion 550, the product and materials included in the plan may be displayed in components portion 560, the determined list of needed scans may be displayed in the scanning task list portion 530, any captured 3D data may be displayed in the captured 3D portion, and a video or image of what is currently in the scanner may be in scanner video portion 510. This is also depicted in FIG. 9. In FIG. 9, portion 910 illustrates an example of video of an object, such as a dental model or dental tray, placed in a scanner. Portion 920 illustrates 3D data as it is being captured from the 3D scanner. Additionally, in some embodiments, as depicted in portion 930, the progress or state of various scanning tasks may be displayed. For example, in portion 930, the scan for a preparation at tooth position 25 is "Ready," the scan for a preparation at tooth position 27 is "Scanning," and the scan for the a gum at tooth position 26 is "Waiting," meaning that it has not yet started.

Figure 1:
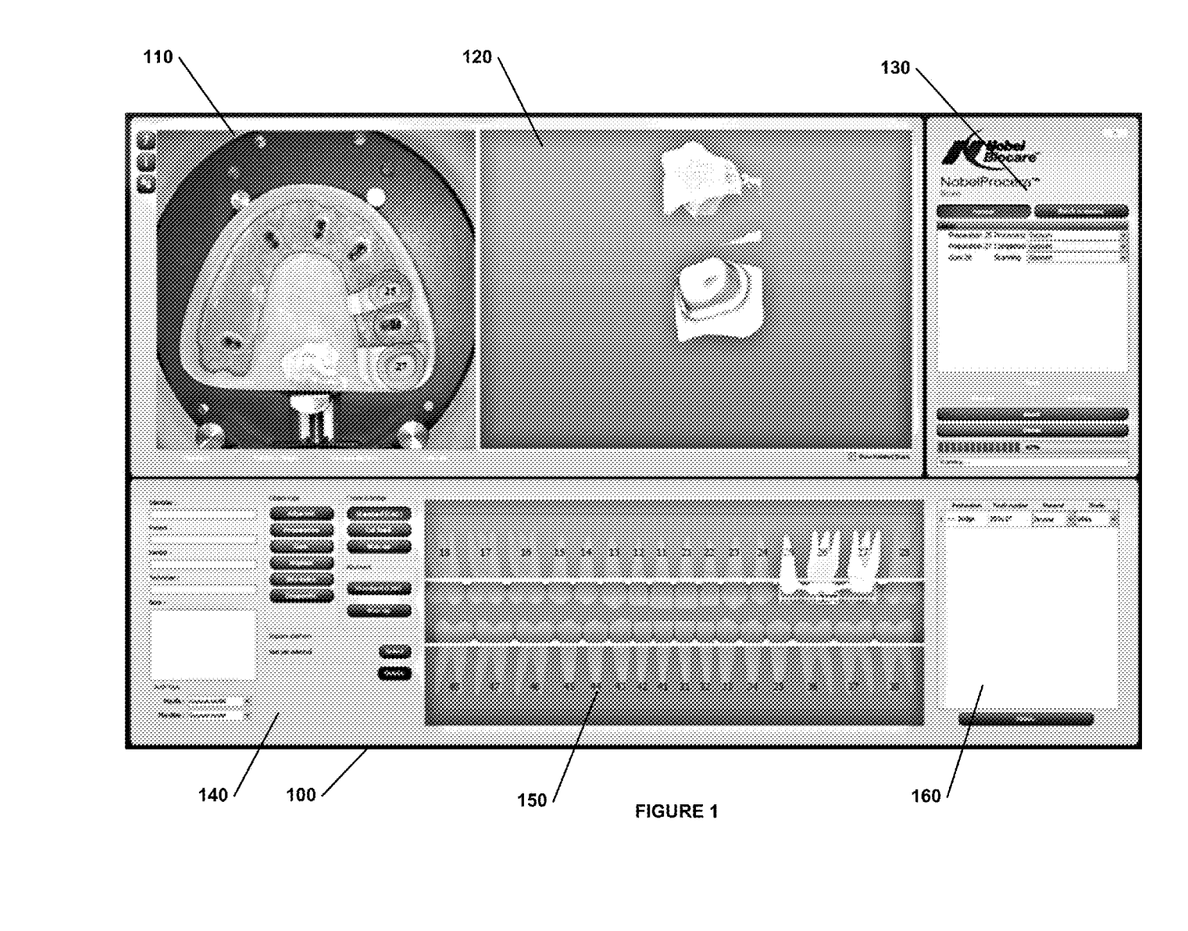
FIG. 1 is an illustration of a first exemplary display for dental data planning.

Further, in some embodiments, if one 3D model of a first part of a situation or dental data plan has already been scanned, then that 3D model of the previously-scanned part (gum, preparation, etc.) may also be displayed in the captured 3D portion. This is depicted in FIG. 1. As depicted in portion 120, the previously-captured and processed 3D model for one preparation is displayed while performing the 3D scan of the second preparation. This is also reflected in the statuses presented in portion 130. The specific area or volume to scan for each tooth position may be suggested or estimated by the system. This is depicted in FIG. 1 with the circles labeled 25, 26, and 27. In some embodiments, the circles may also be moved or modified (such as being resized) by the operator.

The steps of method 400 are not the only possible steps, nor does the order represent the only order available. For example, there may also be a separate step for scanning what is currently in the scanner and, perhaps also, for making a 3D model of scanned data. This may happen at any time during the method 400. Additionally, the order of the steps may be different. For example, the necessary scanning steps may be determined before or after a determination is made whether the plan is valid. In some embodiments, as an additional step, the products used in a design may also be ordered directly from or by the system, said orders going to a supplier or distributor. In those embodiments, constraints, including product availability, may be checked when the product is ordered. Also, the determined information may be displayed at regular intervals and may not await the completion of the steps shown to precede it.

Batch Dental Data Planning

Figure 6:
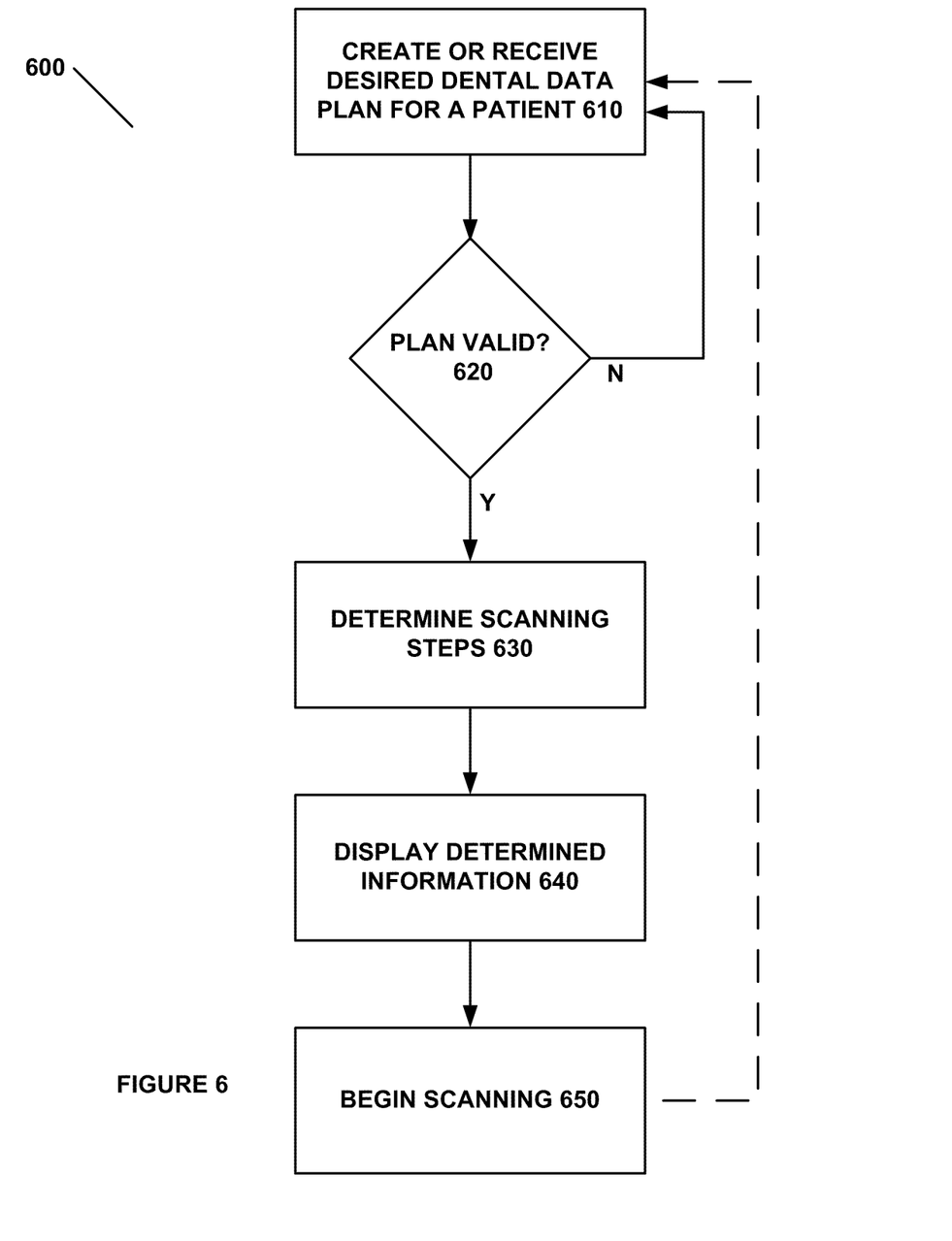
FIG. 6 illustrates a flow diagram for a second exemplary method dental data planning.

FIG. 6 illustrates a flow diagram for a second exemplary method 600 for performing the steps of dental data planning. Some of the steps of method 600 are similar, but not identical to those in method 400. The description herein will reference method 400 and highlight the differences between method 600 and method 400. Generally, method 600 allows an operator to design dental data plans for multiple patients in a manner similar to that in method 400 and also to consolidate the scanning, and sequence and parallelize certain aspects of the process. The sequencing and parallelization may improve the efficiency of operators and the process of dental data planning in general. Such planning may be called "batch" dental data planning or batch case designing.

The operator may design a plan for each patient in step 610 and may do so by working on the case design for each patient, one patient at a time. As noted herein, each case design may start as an empty or blank plan or may start as a default or template. The plan for a particular patient may also be based on the plan for a previous patient. The operator may be able to move among and modify the various dental data plans, or add dental data plans for patients, in the patient information portion 540. The interface for the patient information portion may include a tab for each patient and a tab to create a new patient, as depicted, for example, as tabs 841 in FIG. 8. In some embodiments, any action performable for a single patient, described in part herein with respect to step 410, is available in step 610.

In some embodiments, only a subset of operations described in step 410 are available for batch dental data planning. For example, batch dental data planning may be limited to designing single-unit prosthetics or even be limited to a single type of prosthetic in order to specialize the system for use by those who design many single-tooth plans for multiple patients. This may be more efficient in these scenarios because the interface will not have numerous buttons that would not be used by and might distract the operator. In some embodiments, the indication of which buttons and operations are presented to an operator may be set in a configuration file, a command-line prompt, by selecting a button or hot key on the display (not pictured), or may be coded into the application.

In step 620, as each plan is modified or upon some other action, such as a button press, occurrence of a hardware or software interrupt or event, or the passage of a certain amount of time, a check is made to determine whether the plan is valid. Checking validity of a plan is discussed herein with respect to step 420. If the plan is not valid, an indication may be given to the operator and the operator may modify the plan again in step 610. If the plan is valid, then in step 630, the scanning steps needed for the plan may be determined. This is discussed generally with respect to step 430.

Figure 10:
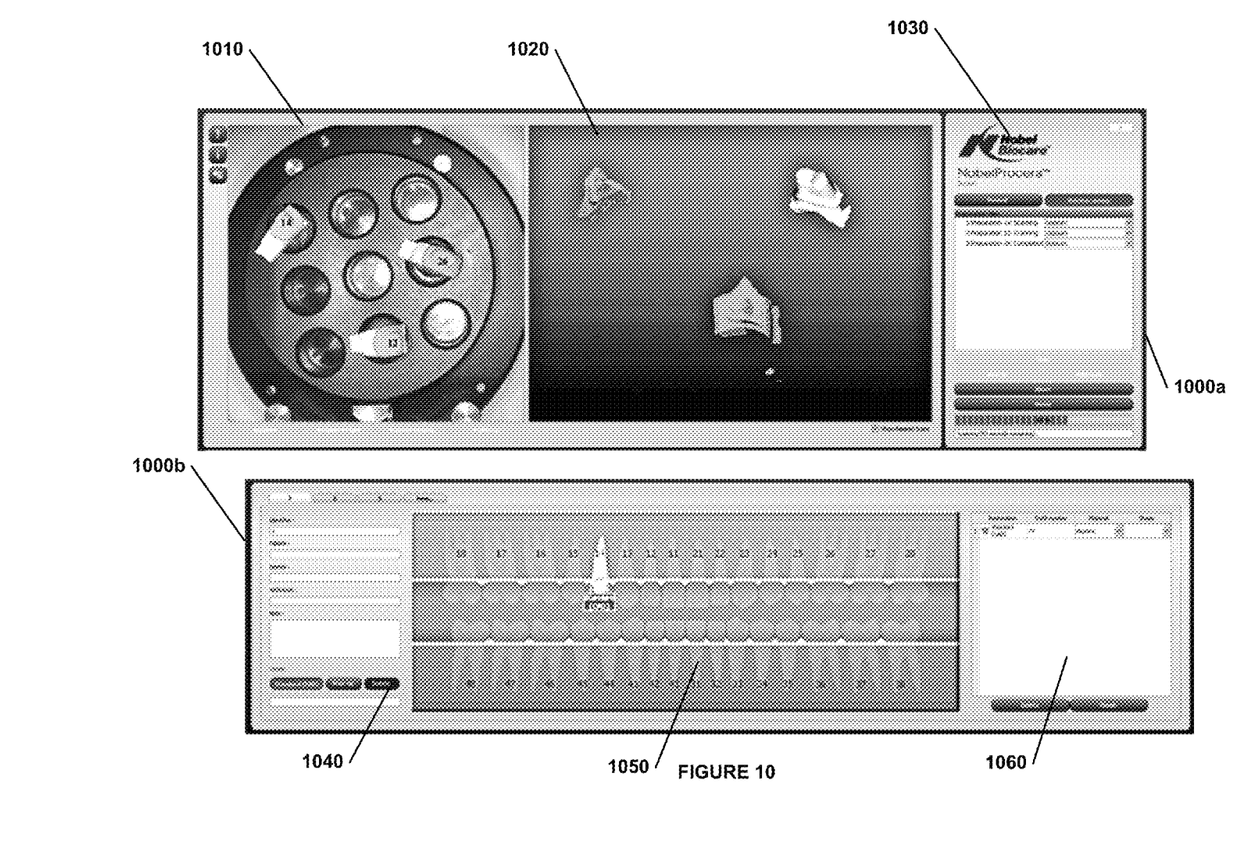
FIG. 10 is an illustration of a seventh exemplary display for dental data planning.

The information determined in the various steps is displayed in step 640. As discussed herein, this may happen after the plan has been validated and the scanning steps have been determined in steps 620 and 630, or it may happen continuously or as any information is updated. In some embodiments, the plan for only a single patient of the multiple patients is displayed in portion 550. In some embodiments, the plan for more than a single patient is displayed. In some embodiments, the operator can control which patient's plan is displayed by selecting that patient (by clicking on a tab, e.g.) in the patient information portion 540. Additionally, as illustrated in FIG. 10, in various embodiments, portions may be separated on two separate displays. In the example of FIG. 10, portions 1010-1030 may be shown on a first display 1000a and portions 1040-1060 may be shown on a second display 1000b. In other embodiments, the portions may be variously distributed across any number of displays.

In step 650, scanning begins. The scanning may begin once the operator has selected a button indicating that the scanning should begin. In some embodiments, the scanning may begin as soon as the plan for a single patient has been finished. For example, the scanning may begin once a plan for a patient has been validated. In various embodiments, after the operator has started scanning for one patient, the operator may recommence and begin or continue designing dental data plans for other patients, as indicated by the dotted line from step 650 to step 610. In some embodiments, after scanning has begun or after scanning has finished, the operator may use a separate dental planning program to add to or further refine, manipulate, or modify the dental data.

In some embodiments, a 3D model may be generated as an object is scanned (see, e.g., FIG. 2, portion 220) and more than one object may be scanned at the same time (see, e.g., FIG. 2, portion 220). Further, in some embodiments, previously-scanned and processed portions of a dental data plan may be displayed as an operator is scanning the next portion of the batch (see, e.g., FIG. 10, portion 1020).

The processes, computer readable medium, and systems described herein may be performed on various types of hardware, such as computer systems. In computer systems may include a bus or other communication mechanism for communicating information, and a processor coupled with the bus for processing information. A computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The computer system may also be coupled to a display, such as a CRT or LCD monitor. Input devices 330 may also be coupled to the computer system. These input devices 330 may include a mouse, a trackball, or cursor direction keys. Computer systems described herein may include the computer 310, display 320, scanner 350, and/or input devices 330. Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor.

As will be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described herein may be embodied in, and fully automated via, software code modules executed by one or more general purpose computers or processors, such as those computer systems described herein. The code modules may be stored in any type of computer-readable medium or other computer storage device. Some or all of the methods may alternatively be embodied in specialized computer hardware.

It should be emphasized that many variations and modifications may be made to the herein-described embodiments, the elements of which are to be understood as being among other acceptable examples. All such modifications and variations are intended to be included herein within the scope of this disclosure and protected by the following claims.

What is claimed is:

1. A method of dental data planning, comprising:
    receiving, from an operator, at a computer system, via a computer-implemented user interface, information about a desired dental data plan for a dental restoration for a patient, wherein the information comprises a location of a prosthetic element to be placed in a mouth of the patient;

determining, with the computer system, whether the desired dental data plan is valid;

when the desired dental data plan is valid, determining, with the computer system, scanning steps necessary for the desired dental data plan, wherein determining, with the computer system, scanning steps necessary for the desired dental data plan, comprises determining the steps of scanning a dental model and determining the steps of scanning the dental model while the dental model has been augmented by adding an object to the dental model as necessary for the desired dental data plan;

displaying, on a first portion of one or more displays coupled to the computer system, the desired dental data plan, and on a second portion of the one or more displays coupled to the computer system, the scanning steps necessary for the desired dental data plan;

wherein displaying, on the second portion of the one or more displays coupled to the computer system, the scanning steps necessary for the desired dental data plan, comprises displaying in the second portion of the one or more displays a step of scanning a dental model in at least the location corresponding to the prosthetic element and a step of scanning the dental model in at least the location corresponding to the prosthetic element while the dental model has been augmented by adding an object to the dental model;

in response to the displaying a step of scanning a dental model, receiving from a scanner a scan of the dental model; and in response to the displaying a step of scanning the dental model while the dental model has been augmented by adding an object to the dental model, receiving from a scanner a scan of the dental model while the dental model has been augmented by adding an object to the dental model; and displaying in a third portion of the one or more displays the scan received from the scanner.

2. The method of claim 1, wherein the computer-implemented user interface includes a desired dental data plan portion and a patient information portion and wherein receiving information about the desired dental data plan comprises:

receiving an object type via the patient information portion; and receiving one or more tooth positions at which to place the object type via the desired dental plan portion.

3. The method of claim 1, wherein the computer-implemented user interface includes a components portion and wherein receiving information about the desired dental data plan comprises:

receiving a material or product type for a component in the desired dental data plan via the components portion.

4. The method of claim 1, wherein the computer-implemented user interface includes a components portion and wherein receiving information about the desired dental data plan comprises:

receiving shade or color for a component in the desired dental data plan via the components portion.

5. The method of claim 1, wherein the desired dental data plan comprises one or more components at one or more positions and the scanning steps are determined based at least in part on the one or more components at the one or more positions.

6. The method of claim 1, wherein the method further comprises:

receiving from the operator a second dental data plan for a second patient; and displaying an indication that there is a second dental data plan in a portion of the display displaying the scanning steps.

7. The method of claim 1, wherein there is more than one scan in the scanning steps displayed on the one or more displays coupled to the system and the computer system guides the operator through the scans in the scanning steps.

8. The method of claim 1, wherein the method further comprises displaying an image of objects in a scanner in a portion of the display displaying the scanning steps.

9. The method of claim 1, wherein the method further comprises displaying 3D models of scanned objects in a portion of the display displaying the scanning steps.

10. The method of claim 1, wherein the method further comprises displaying patient information in a portion of the display displaying the scanning steps.

11. The method of claim 1, wherein the method further comprises displaying an abstract version of the desired dental data plan in a portion of the display displaying the scanning steps.

12. The method of claim 1, wherein the method further comprises displaying components of the desired dental data plan in a portion of the display displaying the scanning steps.

13. The method of claim 1, wherein the method further comprises displaying, when the plan is not valid, an indication that the plan is not valid in a portion of the display displaying the scanning steps.

14. The method of claim 1, wherein said desired dental data plan includes type and position of a desired dental prosthetic and attributes of the desired dental prosthetic.

15. The method of claim 1, wherein the desired dental data plan comprises one or more materials for a dental prosthetic.

16. The method of claim 1, wherein the desired dental data comprises a component selected from the group consisting of crown, bar, coping, abutment, and bridge framework.

17. The method of claim 1, wherein the information about the desired dental data plan comprises a prosthetic spanning one or more tooth positions and wherein determining whether the desired dental data plan is valid comprises determining whether the prosthetic's span is too great based on the number of tooth positions.

18. The method of claim 1, wherein the information about the desired dental data plan comprises a material being used over an extent of tooth positions and wherein determining whether the desired dental data plan is valid comprises determining whether the extent is too great based on the material.

19. The method of claim 1, wherein the method further comprises selecting, via a computer interface, one or more aspects of the desired dental data plan from an electronic catalog.

20. The method of claim 1, wherein determining whether the desired dental data plan is valid comprises determining whether the desired dental data plan fulfills production constraints.

21. The method of claim 1, wherein determining whether the desired dental data plan is valid comprises checking the limitations of dental design software.

22. The method of claim 1, wherein determining whether the desired dental data plan is valid comprises checking the availability of a product included in the desired dental data plan in a product catalog.

23. The method of claim 1, wherein the object added to the model comprises a wax-up.

24. The method of claim 1, wherein the object added to the model comprises an implant replica.

25. The method of claim 23, further comprising placing the dental model into the scanner.

26. The method of claim 25, further comprising augmenting the dental model and placing the augmented dental model into the scanner.

27. A method of dental data planning, comprising:
receiving, from an operator, at a computer system, via a computer-implemented user interface, information about a desired dental data plan for a dental restoration for a patient, wherein the information comprises a location of a prosthetic element to be placed in a mouth of the patient;
determining, with the computer system, whether the desired dental data plan is valid;
when the desired dental data plan is valid, determining, with the computer system, scanning steps necessary for the desired dental data plan; and
displaying, on a first portion of one or more displays coupled to the computer system, the desired dental data plan, and on a second portion of the one or more displays coupled to the computer system, the scanning steps necessary for the desired dental data plan;
wherein the method further comprises:
receiving from the operator a second dental data plan for a second patient; and
displaying an indication that there is a second dental data plan in the second portion of the one or more displays; and
wherein the second dental data plan has associated with it one or more scanning steps and the method further comprises the computer system guiding the operator through the one or more scans for the second dental data plan while continuing to display information associated with the desired dental data plan and receiving from a scanner the one or more scans for the second dental data plan; and
displaying in a third portion of the display the one or more scans received from the scanner.

28. A system for dental data planning data, comprising:
a scanner; and
a computer system configured to:
receive, from an operator via a computer-implemented user interface, information about a desired dental data plan for a patient;
determine whether the desired dental data plan is valid;
when the desired dental data plan is valid, determine scanning steps necessary for the desired dental data plan, wherein the scanning steps include a precedent step of scanning with a scanner a dental model and a subsequent step of scanning with the scanner the dental model when the dental model has been augmented by adding an object to the dental model, wherein the subsequent step is performed after performing the precedent step;
displaying, on a first portion of one or more displays coupled to the computer system, the desired dental data plan, and on a second portion of the one or more displays coupled to the computer system, the scanning steps necessary for the desired dental data plan,
wherein displaying, on the second portion of the one or more displays coupled to the computer system, the scanning steps necessary for the desired dental data plan, comprises displaying in the second portion of the one or more displays a step of scanning a dental model and a step of scanning the dental model when the dental model has been augmented by adding an object to the dental model;
receiving scanned data of the dental model and the dental model when it has been augmented by adding an object to the dental model; and
displaying in a third portion of the one or more displays the scan received from the scanner.

29. The system of claim 28, wherein the computer-implemented user interface includes a desired dental data plan portion and a patient information portion and wherein receiving information about the desired dental data plan comprises:
receiving an object type via the patient information portion; and
receiving one or more tooth positions at which to place the object type via the desired dental plan portion.

30. The system of claim 28, wherein the computer-implemented user interface includes a components portion and wherein receiving information about the desired dental data plan comprises:
receiving a material or product type for a component in the desired dental data plan via the components portion.

31. The system of claim 28, wherein the computer-implemented user interface includes a components portion and wherein receiving information about the desired dental data plan comprises:
receiving shade or color for a component in the desired dental data plan via the components portion.

32. The system of claim 28, wherein the desired dental data plan comprises one or more components at one or more positions and the scanning steps are determined based at least in part on the one or more components at the one or more positions.

33. The system of claim 28, wherein the system is further configured to:
receive from the operator a second dental data plan for a second patient; and
display an indication that there is a second dental data plan in a portion of the display displaying the scanning steps.

34. The system of claim 28, wherein there is more than one scan in the scanning steps displayed on the one or more displays coupled to the system and the computer system guides the operator through the scans in the scanning steps.

35. The system of claim 28, wherein the system is further configured to display an image of objects in a scanner in a portion of the display displaying the scanning steps.

36. The system of claim 28, wherein the system is further configured to display 3D models of scanned objects in a portion of the display displaying the scanning steps.

37. The system of claim 28, wherein the system is further configured to display patient information in a portion of the display displaying the scanning steps.

38. The system of claim 28, wherein the system is further configured to display an abstract version of the desired dental data plan in a portion of the display displaying the scanning steps.

39. The system of claim 28, wherein the system is further configured to display components of the desired dental data plan in a portion of the display displaying the scanning steps.

40. The system of claim 28, wherein the system is further configured to display, when the plan is not valid, an indication that the plan is not valid in a portion of the display displaying the scanning steps.

41. The system of claim 28, wherein said desired dental data plan includes type and position of a desired dental prosthetic and attributes of the desired dental prosthetic.

42. The system of claim 28, wherein the desired dental data plan comprises one or more materials for a dental prosthetic.

43. The system of claim 28, wherein the desired dental data comprises a component selected from the group consisting of crown, bar, coping, abutment, and bridge framework.

44. The system of claim 28, wherein the information about the desired dental data plan comprises a prosthetic spanning one or more tooth positions and wherein determining whether the desired dental data plan is valid comprises determining whether the prosthetic's span is too great based on the number of tooth positions.

45. The system of claim 28, wherein the information about the desired dental data plan comprises a material being used over an extent of tooth positions and wherein determining whether the desired dental data plan is valid comprises determining whether the extent is too great based on the material.

46. The system of claim 28, wherein the system is further configured to select, via a computer interface, one or more aspects of the desired dental data plan from an electronic catalog.

47. The system of claim 28, wherein determining whether the desired dental data plan is valid comprises determining whether the desired dental data plan fulfills production constraints.

48. The system of claim 28, wherein determining whether the desired dental data plan is valid comprises checking the limitations of dental design software.

49. The system of claim 28, wherein determining whether the desired dental data plan is valid comprises checking the availability of a product included in the desired dental data plan in a product catalog.

50. The system of claim 28, wherein the object added to the model comprises a wax-up.

51. The system of claim 28, wherein the object added to the model comprises an implant replica.

52. The system of claim 28, wherein the system is configured to prompt placing the dental model into the scanner.

53. The system of claim 52, further comprising prompting augmenting the dental model and placing the augmented dental model into the scanner.

54. A system for dental data planning data, comprising:
a scanner; and
a computer system configured to:
receive scanned data from the scanner;
receive, from an operator via a computer-implemented user interface, information about a desired dental data plan for a patient;
determine whether the desired dental data plan is valid;
when the desired dental data plan is valid, determine scanning steps necessary for the desired dental data plan; and displaying, on a first portion of one or more displays coupled to the computer system, the desired dental data plan, and on a second portion of the one or more displays coupled to the computer system, the scanning steps necessary for the desired dental data plan; and
wherein the system is further configured to:
receive from the operator a second dental data plan for a second patient; and
display an indication that there is a second dental data plan in the second portion of the one or more displays;
wherein the second dental data plan has associated with it one or more scanning steps and the system is further configured to guide the operator through the one or more scans for the second dental data plan while continuing to display information associated with the desired dental data plan; and
displaying in a third portion of the one or more displays the scan received from the scanner.

55. A non-transitory computer-readable medium for dental data planning data, said computer-readable medium containing non-transitory computer readable instructions, said instructions operable to execute on a computer system, said instructions when executing on the computer system performing a method comprising:
receiving, from an operator, at the computer system, via a computer-implemented user interface, information about a desired dental data plan for a patient;
determining, with the computer system, whether the desired dental data plan is valid;
when the desired dental data plan is valid, determining, with the computer system, scanning steps necessary for the desired dental data plan, wherein the scanning steps include a precedent step of scanning with a scanner a dental model and a subsequent step of scanning with the scanner the dental model when the dental model has been augmented by adding an object to the dental model, the object being necessary for the desired dental data plan;
displaying, on a first portion of one or more displays coupled to the computer system, the desired dental data plan, and on a second portion of the one or more displays coupled to the computer system, the scanning steps necessary for the desired dental data plan;
wherein displaying, on the second portion of the one or more displays coupled to the computer system, the scanning steps necessary for the desired dental data plan, comprises displaying in the second portion of the one or more displays a step of scanning a dental model and a step of scanning the dental model while the dental model has been augmented by adding an object to the dental model;
receiving scanned data of the dental model and the dental model when it has been augmented by adding an object to the dental model; and
displaying in a third portion of the one or more displays the scan received from the scanner.

* * * * *